United States Patent
Triva

(10) Patent No.: US 8,317,728 B2
(45) Date of Patent: *Nov. 27, 2012

(54) METHOD OF USING FLOCKED SWAB FOR COLLECTING BIOLOGICAL SPECIMENS

(75) Inventor: Daniele Triva, Bovezzo (IT)

(73) Assignee: Copan Italia S.p.A., Brescia (IT)

( * ) Notice: Subject to any disclaimer, the term of this patent is extended or adjusted under 35 U.S.C. 154(b) by 0 days.

This patent is subject to a terminal disclaimer.

(21) Appl. No.: 12/903,921

(22) Filed: Oct. 13, 2010

(65) Prior Publication Data

US 2011/0028861 A1    Feb. 3, 2011

Related U.S. Application Data

(63) Continuation of application No. 10/543,873, filed as application No. PCT/EP2004/003392 on Mar. 31, 2004, now Pat. No. 8,114,027.

(30) Foreign Application Priority Data

Apr. 1, 2003 (IT) .............................. MI2003A0643

(51) Int. Cl.

| | |
|---|---|
| A61B 5/00 | (2006.01) |
| B65D 81/00 | (2006.01) |
| A61M 35/00 | (2006.01) |
| C12M 1/00 | (2006.01) |
| C12N 3/00 | (2006.01) |

(52) U.S. Cl. ..................... 600/573; 600/582; 435/283.1; 435/307.1; 604/1

(58) Field of Classification Search .................. 600/562, 600/569, 572, 573; 604/1–3; 132/218, 318; 131/245; 15/103.03, 104.05, 104.16, 104.2; 435/283.1, 307.1; 436/810

See application file for complete search history.

(56) References Cited

U.S. PATENT DOCUMENTS

| | | | |
|---|---|---|---|
| 3,163,160 | A | 12/1964 | Cohen |
| 4,707,450 | A | 11/1987 | Nason |
| 4,749,655 | A | 6/1988 | Corasaniti et al. |
| 4,767,398 | A | 8/1988 | Blasius, Jr. |
| 4,877,036 | A | 10/1989 | Saint-Amand |
| 4,877,037 | A * | 10/1989 | Ko et al. ........................ 600/569 |
| 4,922,936 | A | 5/1990 | Buzzi et al. |
| 5,009,846 | A | 4/1991 | Gavet et al. |
| 5,091,153 | A * | 2/1992 | Bachand ........................ 422/411 |
| 5,623,941 | A | 4/1997 | Hedberg et al. |
| 5,627,071 | A | 5/1997 | Triva |
| 5,738,643 | A | 4/1998 | Stredic, III |
| 5,944,519 | A | 8/1999 | Griffiths |
| 6,010,462 | A | 1/2000 | Stoermer, III |
| 6,232,567 | B1 | 5/2001 | Bonino et al. |
| 6,286,246 | B1 | 9/2001 | Rachal et al. |
| 6,352,513 | B1 | 3/2002 | Anderson et al. |

(Continued)

FOREIGN PATENT DOCUMENTS

| | | |
|---|---|---|
| CN | 1070850 | 4/1993 |
| CN | 2479505 | 2/2002 |
| CN | 2554995 | 6/2003 |

*Primary Examiner* — Max Hindenburg
*Assistant Examiner* — John Pani
(74) *Attorney, Agent, or Firm* — Fish & Richardson P.C.

(57) ABSTRACT

The present invention relates to a swab for collecting biological specimens of the type consisting of a rod terminating in a tip covered with fiber with hydrophilic properties to allow absorption of said specimens, wherein said fiber covers said tip in the form of a layer deposited by flocking.

15 Claims, 1 Drawing Sheet

U.S. PATENT DOCUMENTS

| | | |
|---|---|---|
| 6,413,087 B1 | 7/2002 | Petrich et al. |
| 6,450,810 B1 | 9/2002 | Fischer et al. |
| 6,494,856 B1 | 12/2002 | Zygmont |
| 2003/0108846 A1 | 6/2003 | Hoertsch |
| 2004/0158188 A1 | 8/2004 | Kauffmann et al. |
| 2004/0197730 A1 | 10/2004 | Rowe et al. |

* cited by examiner

METHOD OF USING FLOCKED SWAB FOR COLLECTING BIOLOGICAL SPECIMENS

CROSS REFERENCE TO RELATED APPLICATIONS

This application is a continuation of and claims the benefit under 35 U.S.C. §120 of U.S. patent application Ser. No. 10/543,873, entitled "Swab for Collecting Biological Specimens," filed Jul. 28, 2005, now U.S. Pat. No. 8,114,027, that claims priority under 35 U.S.C. §365 of PCT/EP2004/003392 filed Mar. 31, 2004, and that claims priority under 35 U.S.C. §119 of Italian Application No. MI2003A000643 filed Apr. 1, 2003. Applicant incorporates the disclosure of all three applications by reference herein.

FIELD OF THE INVENTION

The present invention relates to a swab for collecting biological specimens.

BACKGROUND OF THE INVENTION

In the field of clinical and diagnostic analyses, swabs for collecting biological specimens of organic material are known, consisting essentially of a cylindrical rod around one end of which, known as the tip, is wrapped a wad of fibre such as rayon or a natural fibre such as cotton, with hydrophilic properties to allow rapid absorption of the quantity of specimen to be collected and tested. Stable adherence of the fibre wrapped around the tip of the rod is generally achieved by gluing.

Usually, especially if the specimen is to be examined by culturing the microorganisms gathered with the collection, a swab is immersed in a test-tube containing culture medium immediately after collection for appropriate conservation of the specimen during storage and/or transport thereof to the analytical laboratory.

An example of this type of device is given in patent EP0643131 by the same Applicant and refers to a swab for collecting and in vitro transporting specimens, of the type comprising a test-tube with culture medium in gel form and a rod carrying at one end a stopper for sealing the test-tube and at the opposite end means for collecting said specimen, for example a wad of fibre wrapped around the tip of the rod, to be dipped into the culture medium.

The tip of the cylindrical rod, generally manufactured from essentially rigid material such as plastic, for example by extrusion, commonly presents a truncating cut which would make it difficult to insert the swab rod into the cavities (oral, nasal, ocular or rectal, urethral, vaginal etc,) of the patient from whom the specimen is taken, if the tip is not adequately protected. Therefore, the wad of hydrophilic fibre wrapped around said truncated end must not only contain sufficient material to allow absorption of the specimen in the desired quantity, in general 100 microliters, but must also have a sufficiently thick and rounded shape to sheathe the edge of the truncated end so that it cannot cause damage or irritation to the patient during specimen collection. For this reason the fibre wad is wrapped around the tip of the rod in a rounded shape, typically developing into an ogive or similar shape so that it gradually becomes thicker towards the end of the rod thus reaching maximum thickness and therefore maximum protective effect, precisely around the truncated end. A wad of such a shape, while protecting the patient from any risk of contact with said truncated end of the rod, results in a number of drawbacks. The main one is that the thickness of the wad, because of the hydrophilic nature of the fibre, leads to penetration of collected liquid specimen into the mass of said wad. As, for practical reasons, the sample is released from the swab at the moment of analysis by simply gripping the rod of the swab and delicately sliding its tip and hence the fibre impregnated with liquid, along for example a petri dish with culture medium, in practice by spreading the specimen onto this latter (swabbing), even if this operation is repeated and is careful, it does not enable the entire volume e.g. the 100 ml of absorbed specimen to be released, because that part of it which has penetrated into the interior of the wad in the direction of its tip cannot be pressed out towards the surface and hence released by the swab during this operation Due to this defect, on average only about 40% of the liquid specimen collected can in practice be recovered for analysis. Such loss of specimen translates inevitably into reduced sensitivity of analysis and increased false negatives. In this respect, referring to the aforementioned average specimen loss after swabbing the swab, by testing only the 40 microliters released for swabbing out of the 100 microliters of specimen initially collected, it becomes difficult to establish whether a negative test effectively refers to the absence of the microorganism sought or rather to its non- or insufficient transfer from swab to test plate.

A further problem derived from the bulky fibre wad of a swab of the known art is particularly evident for example in the case of urethral or ocular use of said swab. In these and other particular applications it would actually be even more desirable to be able to minimize swab thickness and hence patient discomfort during collection.

SUMMARY OF THE INVENTION

As a solution to these problems, and also to achieve other advantages which will be apparent from the description, the present invention proposes a swab for collecting biological specimens of the type consisting of a rod terminating with a tip covered in fibre with hydrophilic properties to allow absorption of said specimens, characterised in that said fibre covers said tip in the form of a layer applied by means of flocking.

With the aim of better understanding the characteristics and advantages of the invention, a non-limiting example of a practical embodiment thereof is described hereinafter, with reference to the figures of the accompanying drawings. Said example refers to the case of a swab suitable for both the collection and storage of a biological specimen, and therefore also includes a test-tube containing a culture medium suitable for the collected microorganisms into which the swab is to be immersed after collection, such as for example the type described in the aforementioned patent EP0643131 by the same Applicant.

DETAILED DESCRIPTION OF THE INVENTION

Figure 1:
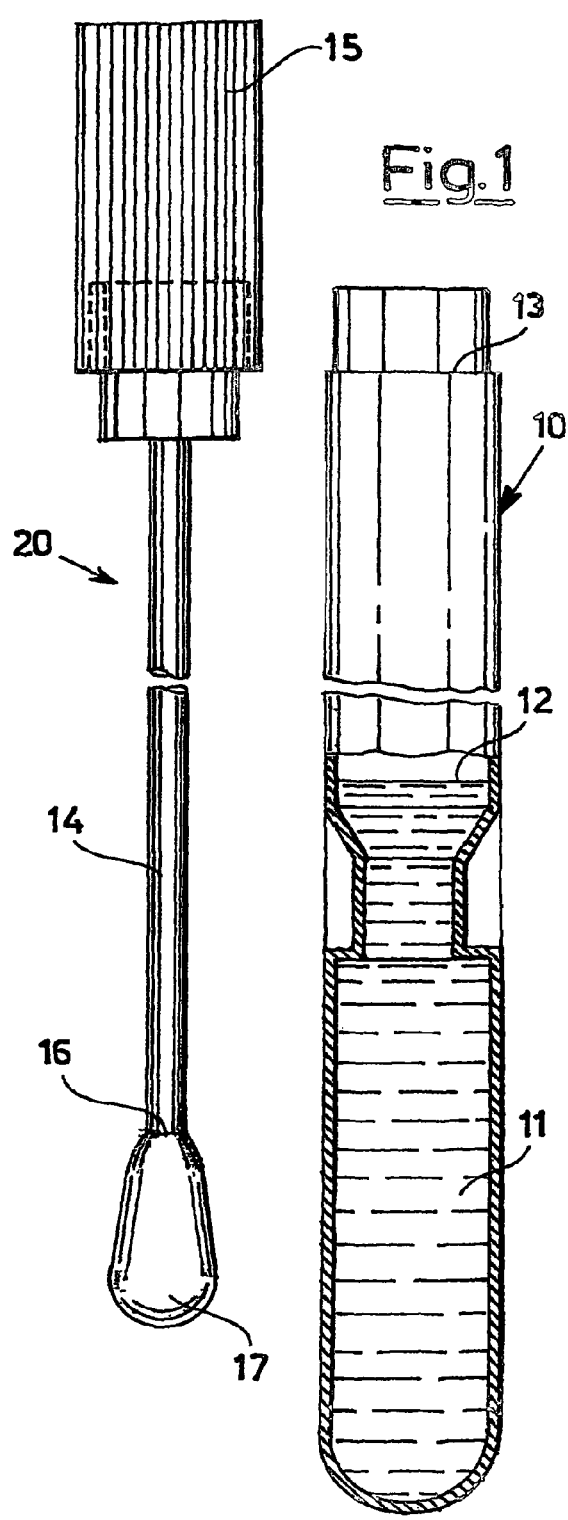
FIG. 1 shows an exploded view of the two components of a device in accordance with the example, that is the swab and test-tube, whereby the test-tube is partially sectioned longitudinally.
Figure 2:
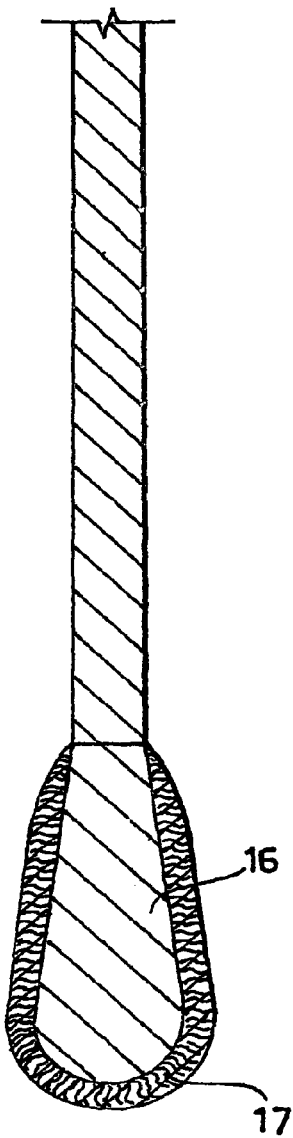
FIG. 2 shows an enlarged detail of the swab of FIG. 1 in section.

With reference to said figures, a device of the invention in accordance with the illustrated example comprises an essentially cylindrical test-tube 10 containing a culture medium in gel form 11, presenting a free surface level 12 inside the test-tube.

The upper open end of the test-tube presents a collar 13 for receiving a closure means.

The device is completed by a swab 20 consisting of a rod 14 carrying at one end a stopper 15 which has to act as the closure means of the test-tube and is hence shaped so that it can engage, for example by snap-engaging, with the collar 13 of the test-tube.

At the opposite end, the rod 14 terminates with a tip 16 carrying a suitable means, for example a layer of fibre 17, for collecting the specimen to be analysed. In the illustrated example, said tip 16 of the rod is shaped in a rounded geometry, similar to an ogive, and said fibre 17 being disposed as a layer of uniform thickness.

In general terms, in accordance with the fundamental characteristic of the invention, said fibre with hydrophilic properties is deposited by means of flocking.

The flocking technique is preferably of the type conducted in an electrostatic field which deposits the fibres in an ordered manner, perpendicular to the surface of the tip of the swab rod, which has been previously coated with adhesive for example by immersion or spraying.

The fibre which is to form the flocked layer is subjected to an electrostatic field, and is hence deposited in an oriented manner and anchored to the surface of the tip, being retained by the adhesive.

The adhesive is preferably water-based: once dried it enables the fibre to be anchored in a stable manner to the swab and to resist abrasion.

The flocked swab is then dried by exposing it to a source of heat or radio-frequency.

The tip of the swab stem is covered with a layer of fibre, preferably of uniform thickness, and from 0.6 to 3 mm thick. The fibre count, i.e. the weight in grams per 100 linear meters of a single fibre, is preferably between 1.7 and 3.3 Dtex. In particular, a fibre of 0.6 mm length and 1.7 Dtex can be applied by flocking to obtain a fine nap, and a fibre up to 3 mm in length and 3.3 Dtex can be applied to obtain a long nap, obtaining, for values intermediate between the aforedefined, corresponding intermediate characteristics of thickness and fineness of the flocked layer.

Within the wide choice of such values, the expedient to be respected according to the objects of the invention is to maintain an ordered arrangement of the fibres, substantially parallel to each other and normal to the surface of the rod, avoiding any overlapping of fibres which can occur if the nap is too long. Indeed, in this manner the capillary represented by each fibre, by virtue of which it can carry out its task of absorbing and releasing essentially the same quantity of specimen, remains unimpaired and functional.

The amount of fibre to be deposited for forming the flocked layer in accordance with the invention is determined on the basis of the type of fibre and the pre-chosen layer characteristics of thickness and fineness, in such a manner as to enable 100 microliters of specimen to be absorbed.

In accordance with the objects of the invention, the fibre is chosen from a wide range of materials provided they are hydrophilic by capillarity, such as for example, synthetic or artificial materials e.g. rayon, polyester, polyamide, carbon fibre or alginate, natural materials e.g. cotton and silk, or mixtures thereof.

EXAMPLES

Some preparative examples are now given of a swab according to the invention. Such examples are not intended in any way to limit the scope of the invention.

Example 1

A swab is prepared using a plastic rod, suitable for human clinical collection, of diameter 2.5 mm which decreases to 1 mm over a length of about 6 cm.

The tip of the part with the smallest diameter is dipped in or sprayed with an adhesive, then the rod is placed vertically in a flocking apparatus in electrostatic field to deposit a polyamide flock.

The polyamide flock of 0.7 mm length and 1.7 Dtex allows 0.5 μl per $mm^2$ to be absorbed, therefore by flocking the 10 mm long tip of said rod the absorbing capacity obtained is 40 μl.

Example 2

Proceeding as per example 1, a rod with a spatulate end is used, suited for example to collecting organic specimens from the oral cavity of a patient. Polyester fibre of 1 mm length and 1.7 Dtex count are used for the flocking.

Example 3

Proceeding as per examples 1 and 2, polyester fibre of 2 mm length and 2.5 Dtex count is used.

Continuing in general terms, it is calculated that a swab of the invention is capable of releasing about 90% of the absorbed specimen by swabbing, in this manner considerably increasing the sensitivity of the analysis compared with swabs of the known art, in particular by almost completely eliminating the risk of false negatives resulting from the incomplete release of the collected specimen from swab to test plate.

In addition, the fact of being able to form, according to the invention, a fibre layer of any thickness, even very small, around the tip of the rod rather than a mass to cover it, as in the known art, means that the required rounded shape of the swab, i.e. free of edges, no longer has to depend on the mass of fibre itself but on the tip of the rod, which can therefore be preferably shaped into a round form, as indeed occurs in the aforedescribed example and shown in the accompanying drawings. Particularly in specific cases where swabs of the greatest possible thinness are required, for example urethral or ocular, this represents a further definite advantage over known swabs. Indeed a swab can be provided with a rounded tip by virtue of its shaping, around which a thin layer of fibre is deposited by flocking to allow on the one hand collection of a sufficient quantity of specimen for analysis, and on the other to minimize the total bulk of the part of the swab which is to penetrate the urethra, in consequence so reducing the discomfort of the patient undergoing the collection procedure.

The shape given to the tip of the swab nevertheless varies greatly according to the type of collection it is intended for, and can even be truncated or have edges when the type of collection (for example oral) allows it.

According to the invention, the type of adhesive, type of fibre and fibre characteristics, such as length and count, are in any case chosen from a wide range of options in order to obtain an ideal specific marker for identifying the microbiological specimen, whether by a direct diagnostic technique, by immuno-test, or by molecular biology techniques such as PCR, or with other known culturing, enrichment or selection techniques.

The specimen to be collected with a swab of the invention generally consists of bacteria or viruses or DNA or RNA or a mixture thereof.

The invention claimed is:

1. A method for collecting a biological specimen to be analyzed, the method being carried out by using a swab comprising a rod terminating in a tip, in which a layer of fibers is disposed by flocking to cover the tip, said layer of fibers having a thickness of 0.6 to 3 mm and a fiber count of 1.7 to 3.3 Dtex, the method comprising collecting a specimen to be analyzed by absorbing a quantity of 40 µl to 100 µl of specimen in said layer of fibers.

2. The method according to claim 1 in which said step of collecting a specimen to be analyzed is carried out by absorbing said quantity of 40 µl to 100 µl of specimen in said layer of fibers by capillarity effect.

3. The method according to claim 1 in which said specimen absorbed in said layer of fibers is a liquid specimen.

4. The method according to claim 1 wherein said specimen comprises a material selected from a group consisting of: bacteria, viruses, DNA, RNA, and a mixture of any of the preceding materials.

5. The method according to claim 1 wherein said quantity of specimen is absorbed in said layer of fibers by capillarity hydrophilic properties of the layer of fibers.

6. The method according to claim 1 in which said fibers are disposed perpendicularly to the surface of the tip by flocking.

7. The method according to claim 1 further comprising the step of storing and transporting said quantity of specimen in said layer of fibers.

8. The method according to claim 1 further comprising a step selected from the group consisting of:
   releasing a quantity of said specimen to be analyzed from said layer of fibers.

9. The method according to claim 1 further comprising the step of analyzing said quantity of liquid specimen after releasing said specimen from said layer of fibers.

10. The method according to claim 1 wherein said fibers define capillaries in said layer of fibers conferring hydrophilic properties by capillarity to the layer of fibers.

11. The method according to claim 1 in which said layer of fibers has capillarity hydrophilic properties and in which said step of absorbing a quantity of liquid specimen in said layer of fibers is carried out by capillarity effect.

12. The method according to claim 1 in which said layer of fibers is of uniform thickness.

13. The method according to claim 1 in which said layer of fibers is disposed on said tip in an ordered arrangement by flocking.

14. The method according to claim 1 further comprising: releasing a quantity of said specimen to be analyzed from said layer of fibers by swabbing.

15. The method according to claim 1 further comprising: releasing, from said layer of fibers, a quantity from 90% to 100% of said specimen absorbed.

* * * * *